United States Patent
Estevez, III

(10) Patent No.: US 8,992,900 B2
(45) Date of Patent: Mar. 31, 2015

(54) SHAVING PROCESS

(75) Inventor: Jose Estevez, III, Hialeah, FL (US)

(73) Assignee: JMDE Holdings Inc., Hialeah, FL (US)

( * ) Notice: Subject to any disclaimer, the term of this patent is extended or adjusted under 35 U.S.C. 154(b) by 0 days.

(21) Appl. No.: 13/609,683

(22) Filed: Sep. 11, 2012

(65) Prior Publication Data

US 2014/0373863 A1 Dec. 25, 2014

(51) Int. Cl.
*A61K 8/19* (2006.01)

(52) U.S. Cl.
USPC .......................................................... 424/73

(58) Field of Classification Search
None
See application file for complete search history.

(56) References Cited

U.S. PATENT DOCUMENTS

| | | | | |
|---|---|---|---|---|
| 3,298,919 A | * | 1/1967 | Todd et al. | 424/47 |
| 5,393,521 A | * | 2/1995 | Lance-Gomez et al. | 424/70.12 |
| 5,443,855 A | * | 8/1995 | Wolf et al. | 424/401 |
| 5,958,394 A | | 9/1999 | Smith | |
| 6,039,937 A | * | 3/2000 | Neubauer | 424/73 |
| 6,660,282 B2 | * | 12/2003 | Crotty et al. | 424/401 |
| 6,974,570 B1 | * | 12/2005 | Griffith | 424/73 |
| 2007/0142845 A1 | * | 6/2007 | Akridge et al. | 606/131 |

OTHER PUBLICATIONS badgerandblade.com forum discussion page on hair conditioner (Aug. 21, 2010).*
badgerandblade.com forum discussion page on baby oil (Apr. 4, 2010).*
badgerandblade.com forum discussion page on isopropyl alcohol (Jul. 12, 2011).*

* cited by examiner

*Primary Examiner* — David J Blanchard
*Assistant Examiner* — Garen Gotfredson
(74) *Attorney, Agent, or Firm* — Jesus Sanchelima, Esq.; Christian Sanchelima, Esq.; Sanchelima & Associates, P.A.

(57) ABSTRACT

A process for shaving that includes the steps of moisturizing the hair, using a sealing agent for sealing the moisture inside the hair keeping the moisture in the hair while smoothing the skin to be shaved applying mineral oil to the hair and skin to create a buffer for the lubricating agent that is applied next. Then, using sufficient water to form a lather. Next, the moisture from the blade after the blade is washed with water by utilizing alcohol. In the final step of the process oil is applied to the blades to prevent contact with the atmospheric moisture and thus extending its useful life.

17 Claims, 3 Drawing Sheets

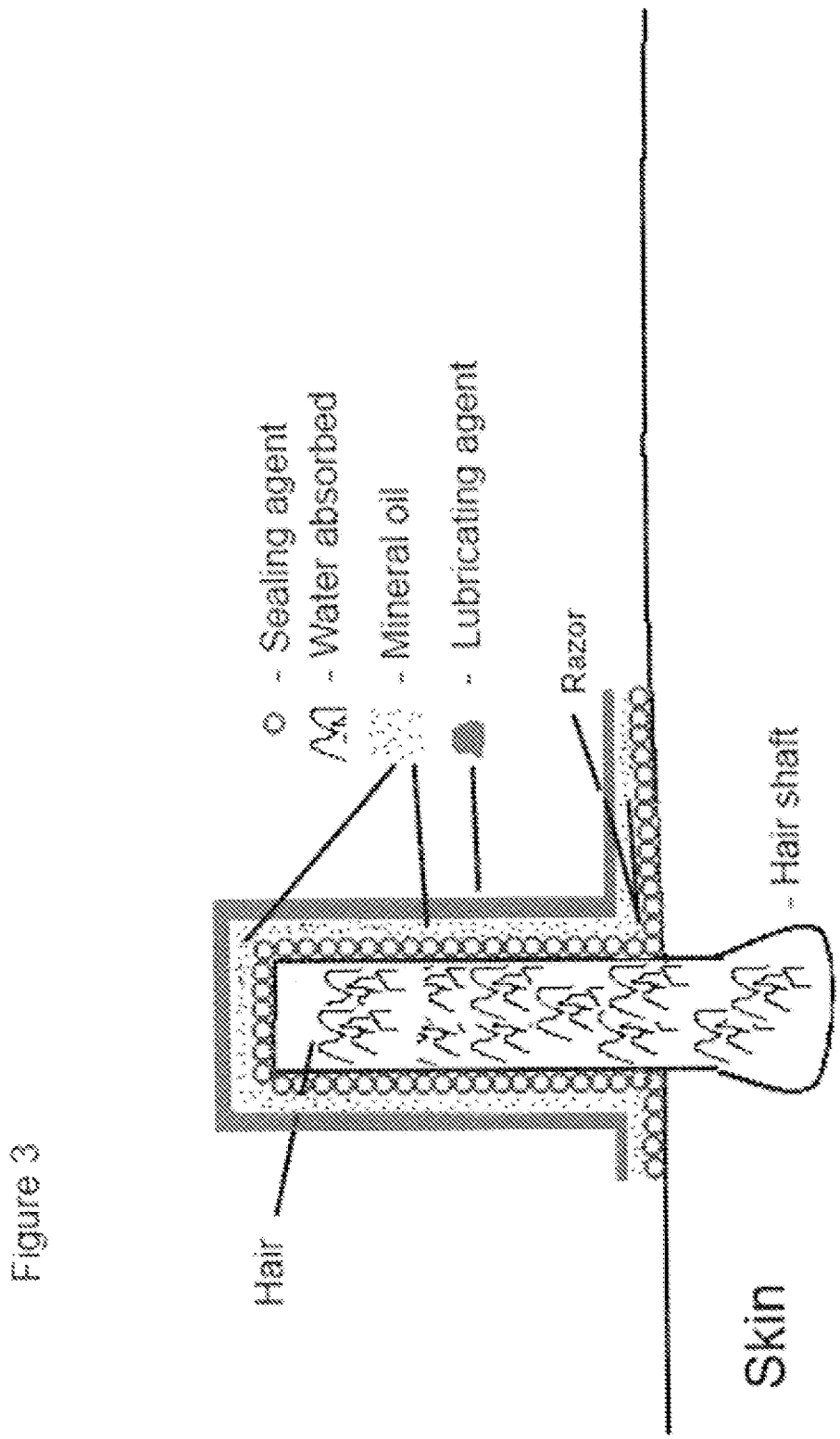

SHAVING PROCESS

BACKGROUND OF THE INVENTION

1. Field of the Invention

The present invention relates to a shaving process or method that extends the useful life of a razor blade, promotes smooth shaving and discourages the reproduction of germs.

2. Description of the Related Art

Several methods for preserving razor blades have been disclosed in the past. None of them, however, include the use of alcohol products, such as ethyl alcohol, for drying out the blades in razors before coating them with oil, such as mineral oil. Nor do previous methods provide for sealing the moisture trapped by the hair, not providing a buffer (oil) for subsequent application of shaving cream.

Applicant believes that the closest reference corresponds to U.S. Pat. No. 6,039,937 issued to Neubauer for a razor conditioner formulation including the use of oil and vitamin E. Neubauer makes a cursory reference to using ethyl alcohol and distilled water to rinse off the salts. See first paragraph of column 3. However, it differs from the present invention because the use of the water with alcohol defeats the purpose for which pure alcohol is used in the present invention, namely, to dry out the blades. If any, the disclosure in Neubauer teaches away form the invention.

Another related reference corresponds to U.S. Pat. No. 5,958,394 issued to Smith for shaving compositions having qualities of pre-shave lubrication, post-shave skin conditioning and blade life extension. Again the reference discloses the use of a water alcohol "mix" that is further combined with a fiber. But does not apply the alcohol separately and subsequent to the use of water. See abstract in Smith's patent. But using the water simultaneously prevents the effective removal of the moisture that will deteriorate the blade.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a shaving process that extends the use of razor blades by reducing, or eliminating, the moisture trapped in the blades that promote their deterioration.

It is another object of this invention to provide a shaving process that avoids nicks and abrasion of the user's skin.

It is still another object of the present invention to provide a shaving process that can be readily implemented by user with readily available ingredients.

It is yet another object of this invention to provide such a process or method that is inexpensive to implement and while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 3 is an elevational cross-sectional representation of the different substances applied to a hair.

DETAILED DESCRIPTION OF THE EMBODIMENTS OF THE INVENTION

Figure 1:
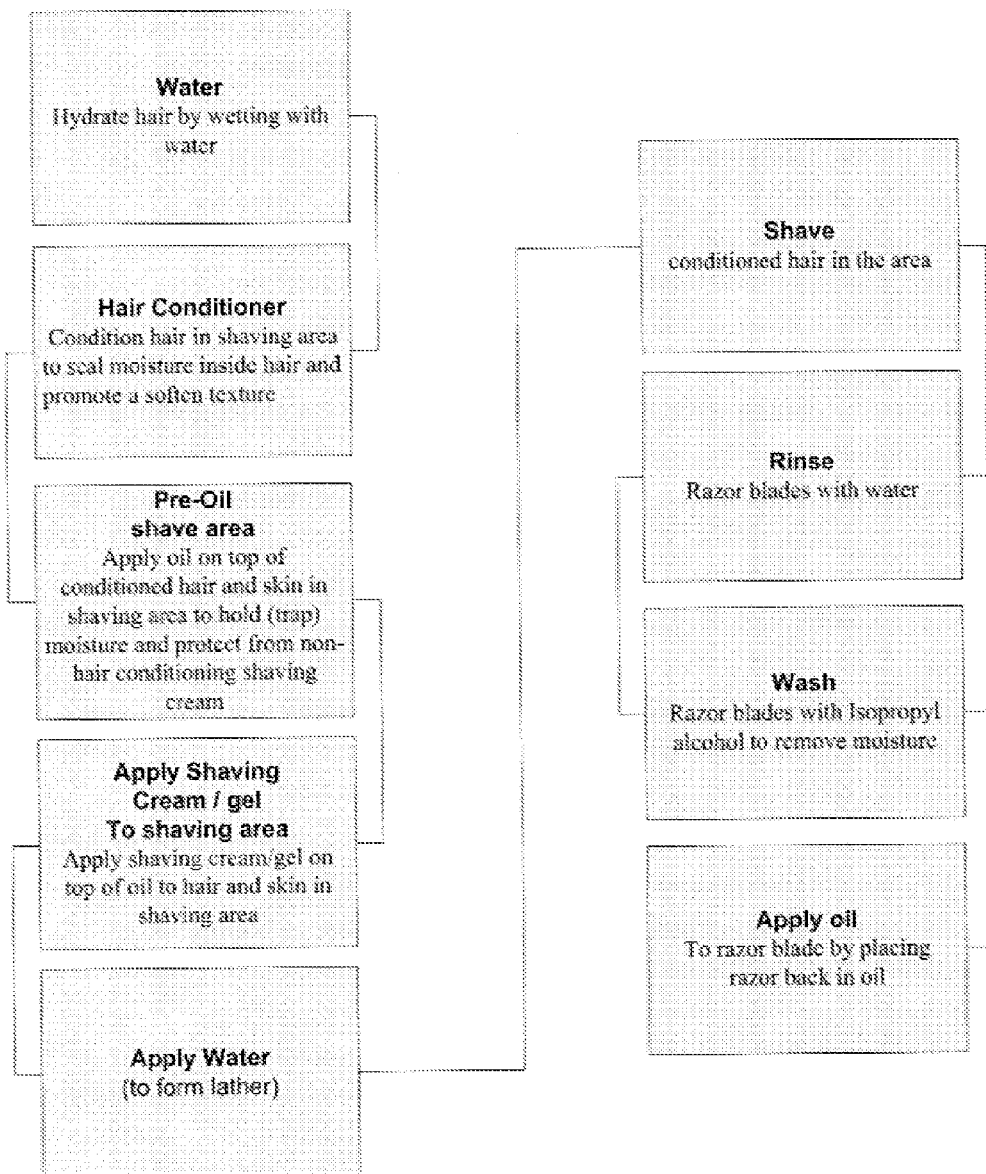
FIG. 1 represents a flowchart illustrating the steps followed in the implementation of the present process.
Figure 2:
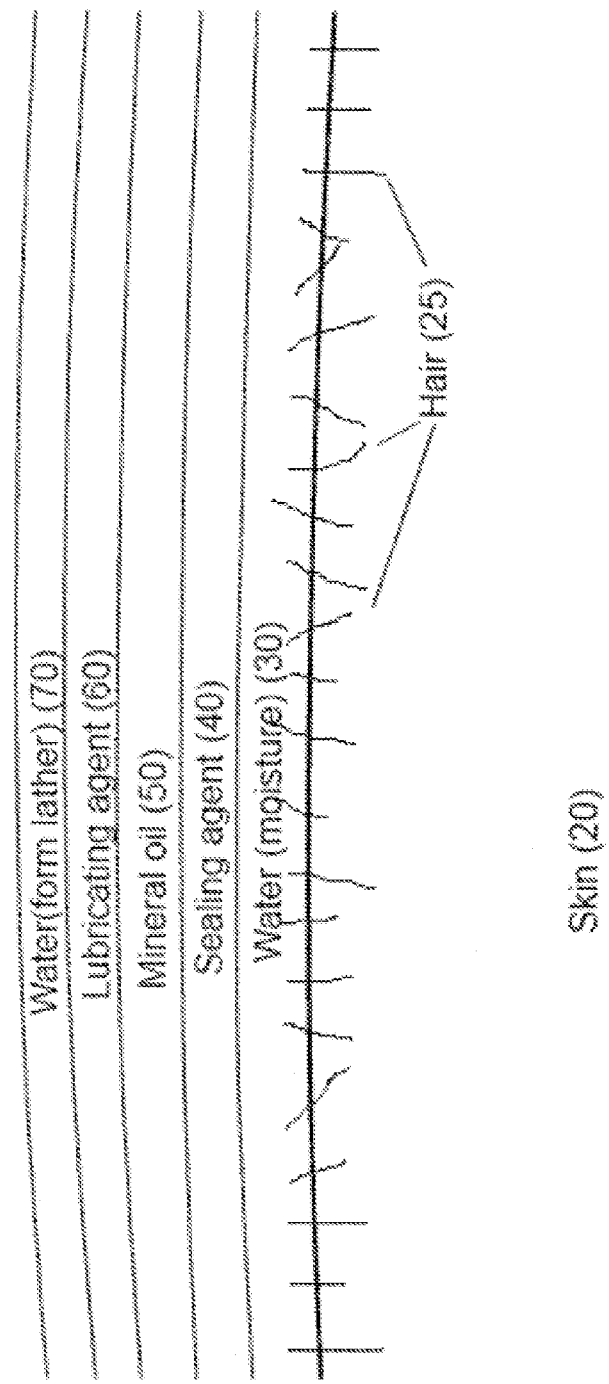
FIG. 2 is an elevational cross-sectional representation of a portion of a targeted skin area where the sequential application of the different substances is represented with broken lines, the latter ones above the earlier ones.

The shaving method subject of the present application includes several steps. In FIG. 1, where a flowchart describing the steps of the process is shown, it can be seen that it includes the following steps:

1) Conditioning the hair and skin in the shaving area by hydrating them thus promoting softening their texture. The hydration is accomplished using regular tap water, (but distilled water can also be used to avoid the entrapment of mineral deposits on or between the blades) to cause moisture to be captured by the hair and skin.

2) Applying a sealing agent, such as a hair conditioner, to the shaving area to seal the moisture inside the hair. This will cause the hair to have a softer texture. For the purposes of this application, suitable hair conditioners will be those compounds that alter the texture of hair making it sufficiently softer than without the hair conditioner and to seal the moisture captured by the hair. Hair conditioner, as known by those skilled in the art, include a base of water or oil and moisturizers, emollients, reconstructors, acidifier, polymers, copolymers, crosspolymers, surfactants, humectants, skin conditioners, antistatic agents and fragrances. The purpose for applying a hair conditioner agent is to seal the hair, which is a tubular body with irregularities on the hair surface where moisture is trapped. The hair conditioner seals the moisture within the hair and skin irregularities. For the purposes of this application, suitable hair conditioners are those that include:

A) Cationic Surfactants. In a concentration range of 500 to 800 ppm (parts per million) and corresponding to 1 to 7% of the weight of the entire hair conditioner composition weight. The following are suitable cationic agents: stearamidopropyl dimethylamine, behenyl amidopropyl dimethylamine glutamate (BAPDMA) and behentrimonium chloride $(CH_3(CH_2)_{21}N(CL)(CH_3)_3$.

B) Dimethicone based silicones including silicone polymers, cross polymers and copolymers. These compounds are used with a concentration range between 200 ppm and 1000 ppm and from 2 to 12% per weight of the resulting compound. A suitable silicone that can be used is PDM blend (dimethicone).

3) Applying mineral oil, optionally with aloe vera and vitamin E, to the conditioned hair and skin in the targeted area to hold (trap) the moisture created through hydration in the previous hydrating step. The oil provides a buffering agent to neutralize the humectants found in shaving creams or gels (to be applied in the next step). The oil will prevent the extraction of moisture from the hair to which it will be exposed in the next step.

4) Applying a lubricating agent, such as shaving creams or gels to the hair and skin in the targeted area to be shaved. By shaving cream or gel will be understood any such products commonly known by these generic terms to lubricate and provide moisture to the hair and to the skin surface. The composition of commercially available shaving creams and gels may include water, humectants, surfactants, emollients, antistatic agents, binding agents, film forming agents, skin conditioner, emulsion stabilizer, viscosity controller agent, and fragrances. For the present invention suitable shaving creams or gels will be water-based compositions that include the following compositions:

A. Surfactants.
  1) Cocamidopropyle Betaine. Between 3% and 5% by weight, and preferably 3% in one of the embodiments.
  2) Sodium Lauryle Sulfate. Between 2.3% and 4% by weight, and preferably 2.3% in one of the embodiments.
  3) Triethanolamine. Between 3.7% and 6% by weight, and preferably 3.7% in one of the embodiments.
  4) Lanolin. Between 5% and 8% by weight, and preferably 5% in one of the embodiments,
  5) Stearic acid 8% and 12% by weight, and preferably 8% in one of the embodiments.
B. Emollient.
  7) Polyoxyethylene sorbitan monostearate between 6 and 7%, by weight, and preferably 6%.
C. Base or carrier.
  8) A base of water for the balance of the weight.
5) Applying water to form sufficient lather to provide a comfortable shave that avoids or minimizes nicks or abrasive contact with a user's skin.
6) Shaving the hair in the targeted area.
7) Rinsing the razor blade(s) with water to dislodge any particles trapped in the vicinity of the blade (s). The use of water, tap or well water, is suitable but a user may optionally use distilled water to reduce the possibility of minerals being lodged in the vicinity of the blades, or the blades themselves.
8) Washing razor blades with alcohol, preferably isopropyl alcohol. This washing step with alcohol may include some mechanical agitation also to ensure that the moisture created in the previous step is removed (the blades are dried out).
9) Applying mineral oil to the razor blades to cover them and prevent moisture from coming in contact with the blades. The application of oil can be accomplished by submerging the razor blades in a vessel containing oil and leaving the blades in contact with the oil for a predetermined amount of time. The oil cover will prevent rusting of the blades. In this manner, the blade's useful life is extended.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A shaving process comprising the steps of;
  A) conditioning hair and skin in a predetermined area of a user's body by hydrating the hair and skin in said area thereby capturing moisture on surfaces of the hair and skin;
  B) subsequently applying an effective amount of a conditioner to seal a substantial portion of said moisture in the hair and skin in said predetermined area;
  C) subsequently applying mineral oil to the hair and skin in said area to hold said moisture on said hair and skin surfaces and to buffer them against the effect of humectants;
  D) subsequently applying a lubricating agent to the hair and skin in said area to provide sufficient lubrication to be combined with water in the next step to allow a razor blade assembly to slide with minimal friction;
  E) subsequently applying water to the hair and skin in said area to form sufficient lather necessary to provide a comfortable shave that avoids or minimizes nicks and abrasive contact of the blade of said razor blade assembly with a user's skin;
  F) subsequently shaving the hair in said predetermined area.

2. The shaving process set forth in claim 1 wherein said conditioner is a hair conditioner.

3. The shaving process set forth in claim 2 wherein said conditioner includes at least one dimethicone based silicone compound.

4. The shaving process set forth in claim 3 wherein said conditioner includes at least one cationic surfactant.

5. The shaving process set forth in claim 4 wherein said conditioner includes dimethicone based silicone compounds in a concentration that ranges from 200 ppm to 1000 ppm and constitutes between 2% and 12% of the weight of the conditioner.

6. The shaving process set forth in claim 5 wherein said conditioner includes cationic surfactants in a concentration that ranges between 500 and 800 ppm and ranging from 1% to 7% of the entire weight of the conditioner.

7. The shaving process set forth in claim 6 wherein said conditioner includes humectants having a concentration range between 1000 and 2000 ppm and corresponding to a portion of the weight of the conditioner that ranges from 12 to 14 percent, and said humectants are selected from a group that consists of stearyl alcohol (C 18OH) and cetyl alcohol (C 16OH).

8. The shaving process set forth in claim 1 wherein said lubricating agent is a shaving cream.

9. The shaving process set forth in claim 8 wherein said lubricating agent includes at least one surfactant compound.

10. The shaving process set forth in claim 9 wherein said lubricating agent includes at least one emollient compound.

11. The shaving process set forth in claim 10 wherein said surfactant in said lubricating agent includes at least one compound from a group consisting of Cocamidopropyl betaine, sodium lauryl sulfate, triethanolamine, lanolin, and stearic acid.

12. The shaving process set forth in claim 11 wherein said emollient in said lubricating agent includes polyoxyethylene sorbitan monostearate.

13. The shaving process set forth in claim 8 wherein said lubricating agent includes at least one surfactant and at least one emollient compound.

14. The shaving process set forth in claim 13 wherein said surfactant in said lubricating agent includes cocamidopropyl betaine between 3% and 5% by weight, sodium lauryl sulfate between 2.3% and 4% by weight, triethanolamine between 3.7% and 6% by weight, lanolin between 5% and 8% by weight, and stearic acid between 8% and 12% by weight.

15. The shaving process set forth in claim 14 wherein said emollient in said lubricating agent includes polyoxyethylene sorbitan between 6% and 7% by weight.

16. The shaving process set forth in claim 1 wherein said lubricating agent includes a shaving cream.

17. The shaving process set forth in claim 16 wherein said conditioner includes cationic surfactants, and dimethicone silicone compounds, and said lubricating agent includes surfactants and emollient compounds.

* * * * *